US006581037B1

(12) United States Patent
Pak

(10) Patent No.: US 6,581,037 B1
(45) Date of Patent: Jun. 17, 2003

(54) SYSTEM AND METHOD FOR ANALYZING HUMAN BEHAVIOR

(75) Inventor: Michael Pak, 90 Meyer Rd. #500, Amherst, NY (US) 14226

(73) Assignee: Michael Pak, Logansport, IN (US)

( * ) Notice: Subject to any disclaimer, the term of this patent is extended or adjusted under 35 U.S.C. 154(b) by 0 days.

(21) Appl. No.: 09/434,982

(22) Filed: Nov. 5, 1999

(51) Int. Cl.[7] .............................................. G06F 17/60
(52) U.S. Cl. ......................................................... 705/1
(58) Field of Search ............................................ 705/1

(56) References Cited

U.S. PATENT DOCUMENTS

| | | | | |
|---|---|---|---|---|
| 4,220,992 A | * | 9/1980 | Blood et al. | 377/26 |
| 5,710,005 A | * | 1/1998 | Rittenburg | 422/56 |
| 5,799,268 A | * | 8/1998 | Boguraev | 382/224 |
| 5,982,932 A | * | 11/1999 | Prokoski | 707/2 |
| 6,026,397 A | * | 2/2000 | Sheppard | 703/6 |
| 6,216,098 B1 | * | 4/2001 | Clancey et al. | 703/22 |
| 6,338,066 B1 | * | 1/2002 | Martin et al. | 707/10 |
| 2001/0011211 A1 | * | 8/2001 | Bushey et al. | 704/10 |

FOREIGN PATENT DOCUMENTS

| | | | | |
|---|---|---|---|---|
| JP | 06035892 A | * | 2/1994 | G06F/15/20 |
| WO | WO 9813775 A1 | * | 4/1998 | G06F/17/50 |

OTHER PUBLICATIONS

Fielo, Sandra C.; Degazon, Cynthia E., "When cultures collide: decision making in a multicultural environment." Nursing and Health Care Perspectives, v18, n5, p238(6).*

* cited by examiner

Primary Examiner—John G. Weiss
Assistant Examiner—Jonathan Ouellette
(74) Attorney, Agent, or Firm—Ned Pejic

(57) ABSTRACT

Systems and methods for understanding human interactive behavior and its interpretation are provided. The systems and methods of the present invention are applicable to the interpretation of interactions between individuals, groups and societies in almost any social setting and time period. In this regard, the present invention provides a culture-based method of predicting human behavior, its interpretation, probability, type and magnitude of response. The method includes, for example, the steps of: identifying a culture to be analyzed; identifying a behavioral communication; associating the identified behavioral communication with a behavioral reference indicia; associating the behavioral reference indicia with a culture-based behavior response indicia indicative of the probability, magnitude, and type of positive or negative behavior response to the identified behavioral communication; associating the behavioral reference indicia with a culture-based interpretation indicia indicative of the probability and magnitude of positive or negative interpretation of the identified behavior; and outputting at least the culture-based behavior response indicia for display. The behavioral reference indicia is classification and identification mechanism by which behaviors having minor or major differences there between may be indexed for database organization. The interpretation indicia is preferably an indicia indicative of the probability and magnitude of positive or negative interpretation of the identified behavior within the culture. The behavior response indicia is preferably indicative of the probability and magnitude of positive or negative behavioral response to the identified behavioral communication. The present invention also determines of the Interpretation Indicia has exceeded a veto threshold.

10 Claims, 6 Drawing Sheets

| CULTURE | BEHAVIOR | BEHAVIORAL REFERENCE INDICIA | INTERPRETATION INDICIA | BEHAVIORAL RESPONSE INDICIA |
|---|---|---|---|---|
| CULTURE 1 | BEHAVIOR 1 | BEHAVIORAL REFERENCE INDICIA 1 | INTERPRETATION INDICIA 1 | BEHAVIORAL RESPONSE INDICIA 1 |
| CULTURE 1 | BEHAVIOR 2 | BEHAVIORAL REFERENCE INDICIA 2 | INTERPRETATION INDICIA 2 | BEHAVIORAL RESPONSE INDICIA 2 |
| CULTURE 1 | BEHAVIOR (N) | BEHAVIORAL REFERENCE INDICIA (N) | INTERPRETATION INDICIA (N) | BEHAVIORAL RESPONSE INDICIA (N) |

SYSTEM AND METHOD FOR ANALYZING HUMAN BEHAVIOR

FIELD OF THE INVENTION

The invention relates generally to tools for studying human behavior, and more particularly, to systems and methods for generating culture-based models of human behavior and the use of such models in predicting human behavior.

BACKGROUND OF THE INVENTION

Behavior is a large component of how humans communicate with each other. In this regard, it is difficult at times to correctly determine the proper meaning or interpretation of a behavioral communication. Closely connected therewith, reactions or responses to interpretations of behavior communication are also difficult to predict. When coupled with cultural differences, the prediction of reactions and responses to behavior become increasingly difficult. This is especially true when individuals or groups of one culture try to communicate, verbally or non-verbally, with individuals or groups of another culture. Such cross-cultural misunderstandings have sometimes been labeled as "culture shock." In such situations, there is often a misunderstanding or misinterpretation of the expressed behavior or communication. As a result such misunderstandings or misinterpretations, improper or disproportionate responses to the expressed behavior may be expressed. The consequences of such improper or disproportionate responses can be serious such as for example, social breakdown or even conflict. Accordingly, systems and methods for predicting human behavior are desirable.

SUMMARY OF THE INVENTION

In accordance with the present invention, systems and methods for understanding human interactive behavior and its interpretation are provided. The systems and methods of the present invention provide for the prediction and interpretation of human behavior and the interpretation of interactions between individuals, groups and societies in almost any social setting and time period. The systems and methods of the present invention also provide for the probability of response to particular behaviors including, for example, the type (i.e., direct or indirect and/or overt or covert response) and magnitude thereof. In this regard, one embodiment of the present invention provides a culture-based method of predicting human behavior. The method includes, for example, the steps of: identifying at least one behavior to be analyzed; identifying a culture's line of interpretation; and identifying the probability of a culture-based behavioral response based on the behavior to be analyzed and the culture's line of interpretation.

According to another embodiment of the present invention, a method for predicting human behavior is provided that includes, for example, the steps of: identifying a culture to be analyzed; identifying a behavioral communication; associating the identified behavioral communication with a behavioral reference indicia; associating the behavioral reference indicia with a culture-based behavior response indicia indicative of the probability and magnitude of positive or negative, direct or indirect, and overt or covert behavior response to the identified behavioral communication; associating the behavioral reference indicia with a culture-based interpretation indicia indicative of the probability and magnitude of positive or negative interpretation of the identified behavior; and outputting at least the culture-based behavior response indicia for display.

The behavior communication may be described by keywords or selected from a predetermined list of behaviors to be analyzed. The behavioral reference indicia is classification and identification mechanism by which behaviors having minor or major differences there between may be indexed for database organization. The interpretation indicia is preferably an indicia indicative of the probability and magnitude of positive or negative interpretation of the identified behavior within the culture. The behavior response indicia is preferably indicative of the probability and magnitude of positive or negative, direct or indirect, and/or overt or covert behavioral response to the identified behavioral communication.

According to another embodiment of the present invention, a system for the culture-based prediction of the probability of direct or indirect behavior in response to an observed behavior is provided. The system includes, for example, a database having at least one cultural description and at least one corresponding behavior description, behavioral reference indicia, and Indirect Behavioral Response Indicia and. logic for predicting the probability of behavior in response to the observed behavior. The logic for predicting the probability of a behavioral response includes, for example, logic for identifying a culture to be analyzed, logic for identifying an observed behavior, logic for associating the identified behavior with a behavioral reference indicia, logic for associating the behavioral reference indicia with a culture-based behavior response indicia indicative of the probability of a behavioral response to the identified behavior, and logic for outputting the culture-based behavior response indicia for display.

Another embodiment of the present invention determines of a veto threshold has been exceeded by the Interpretation Indicia for a particular behavior. Behaviors interpreted as falling below the veto threshold greatly increase the probability of disregard for another party's well being, emotions and decision making when formulating a responsive behavior. This can lead to unmoderated negative responses that can include repeated negative actions that are disproportionate to the offending behavior and/or planning or performing a single overwhelming action designed to extinguish the offending behavior or eliminate the opposing individual or group.

It is therefore an advantage of the present invention to provide a system and method for predicting human behavior that is based on cultural values and interpretations.

It is a further advantage of this invention to provide a system and method for the culture-based prediction of the probability of direct or indirect, covert or overt behavior in response to an observed behavior.

BRIEF DESCRIPTION OF THE DRAWINGS

In the accompanying drawings which are incorporated in and constitute a part of the specification, embodiments of the invention are illustrated, which, together with a general description of the invention given above, and the detailed description given below, serve to example the principles of this invention.

FIGS. 5 is a representative database structure of the present invention.

DETAILED DESCRIPTION OF THE ILLUSTRATED EMBODIMENT

Each interactive human behavior ranging from highly complex cooperative to very antagonistic or negative corresponds to a meaning or interpretation assigned to it by a particular culture. These culture-based interpretations range from very positive such as, for example, love or strong friendship, through neutrality or indifference to very negative such as, for example, disdain or hate. These culture-based interpretations can be broadly subdivided into three categories: positive, neutral, and negative.

Figure 1:
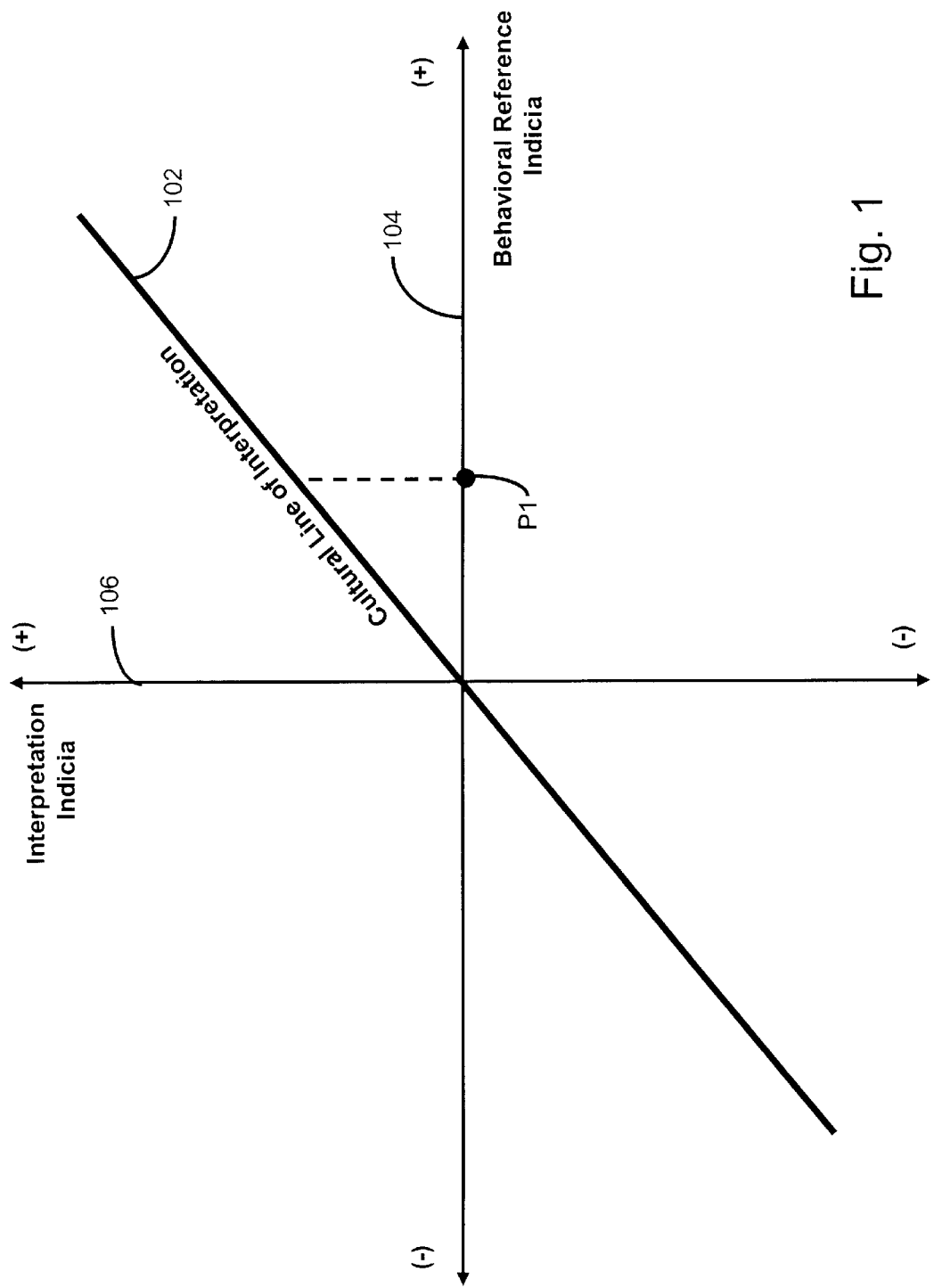
FIG. 1 is a graph illustrating a general cultural line of interpretation of the present invention generated by plotting Behavioral Reference Indicia versus Interpretation Indicia.

Referring now to FIG. 1, when the quantity or intensity of interactive behaviors, as represented by a Behavioral Reference Indicia, is plotted against the corresponding culture-based interpretations, as represented by an Interpretation Indicia, a straight line is obtained that is designated as the cultural line of interpretation 102. Each individual or group in the culture being analyzed interprets the behavior of other individuals or groups and assigns a meaning or interpretation to the behavior based on their own culture. This interpretation is represented by the cultural line of line of interpretation 102. For example, based on the cultural line of interpretation 102 of FIG. 1, a behavior that has a Behavioral Reference Indicia of zero (0) has a corresponding Interpretation Indicia of zero (0). This indicates that meaning or interpretation assigned to the behavior by the culture is neither positive or negative, i.e., neutral. A behavior that has a Behavioral Reference indicia represented by P1 in FIG. 1 has a corresponding positive Interpretation Indicia. That is, the behavior has a positive meaning assigned to it by the culture.

Cultural lines of interpretation are also important because individuals and groups also act toward others with the intent of, for example, establishing relationships based on their own cultural line of interpretation. Therefore, every cultural line of interpretation has a corresponding line of action or reaction, which also corresponds to line 102. The degree of correlation between the cultural line of interpretation 102 and a cultural line of action or reaction relates to the individual's or group's ability to accurately interpret behavior and moderate their actions and reactions.

Figure 2:
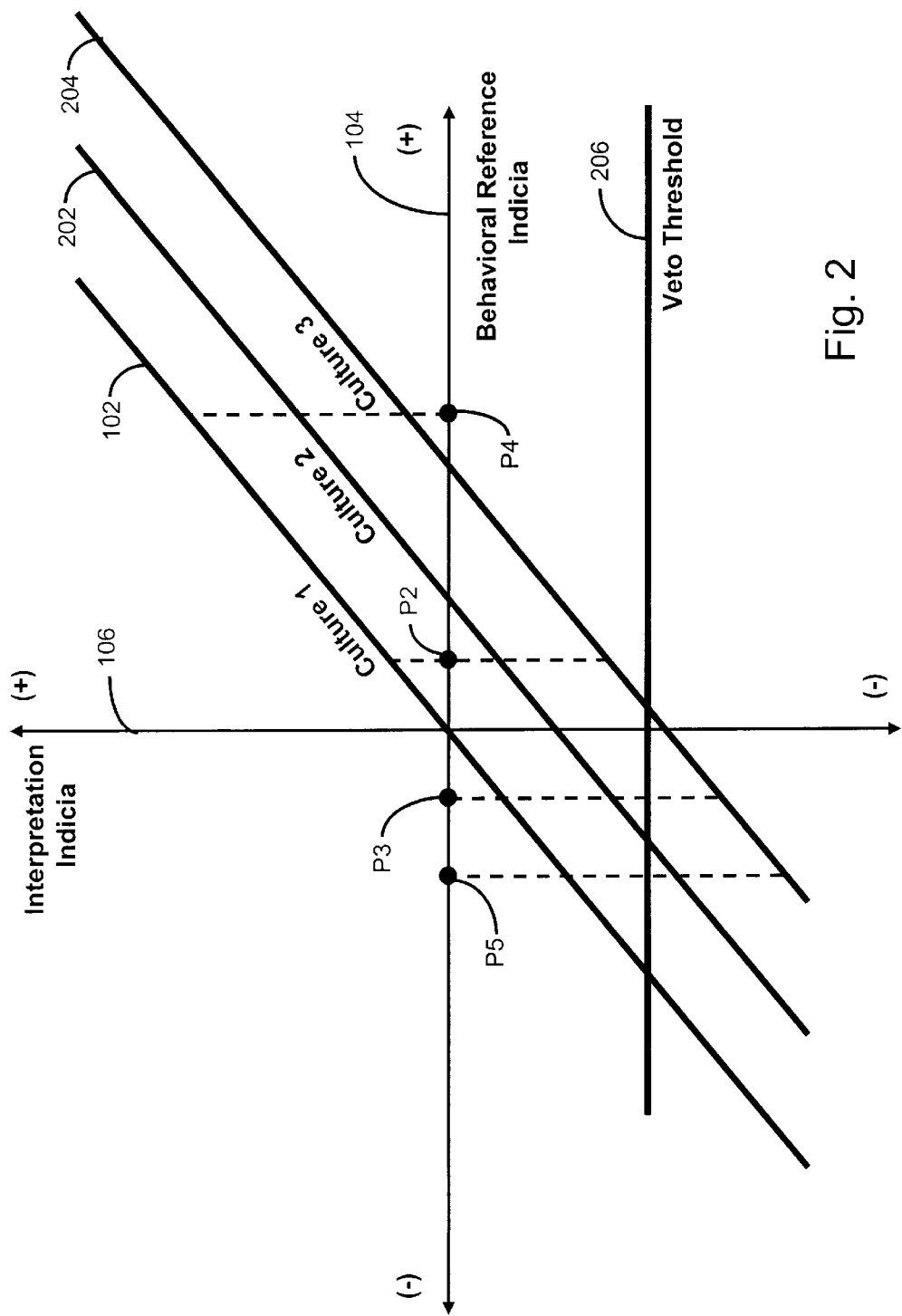
FIG. 2 is a graph illustrating a plurality of cultural lines of interpretation representing different cultures and a veto line threshold.

Depending on the degree of development, extent of competition for resources, historical background, geography, and multiple other socioeconomic and environmental factors, a society's cultural line of interpretation 102 may be shifted from left to right along the horizontal, or Behavioral Reference Indicia axis, as illustrated in FIG. 2. Cultures having perceptibly separated lines of interpretation will have different meanings or interpretations for same behaviors. For example, FIG. 2 shows culture 1 and its cultural line of interpretation 102, culture 2 and its cultural line of interpretation 202, and culture 3 and its cultural line of interpretation 204. These variations in meanings or interpretations of behaviors follow a particular pattern.

In cultures having left-shifted lines of interpretation such as, for example, culture 1 when compared to culture 2, relatively small quantities of positive behavior (as represented by, for example, Behavioral Reference indicia P2) by have a relatively large positive meaning or Interpretation Indicia, while relatively large quantities of negative behavior (as represented by, for example, Behavioral Reference indicia P3) have a relatively small negative meaning or Interpretation Indicia. In cultures having right-shifted lines of interpretation such as, for example, culture 3 when compared to cultures 1 and 2, large quantities of positive behavior (as represented by, for example, Behavioral Reference indicia P4) have a relatively small positive meaning or Interpretation Indicia, while small quantities of negative behavior (as represented by, for example, Behavioral Reference Indicia P5) have a relatively large negative meaning or Interpretation Indicia. Accordingly, in cultures with right-shifted lines of interpretation, behaviors having larger Behavioral Reference Indicia (i.e., very positive behaviors) are required to establish and/or maintain the correspondingly same positive meanings or interpretations than would be required in left-shifted cultures.

Misinterpretation of behavior and dysfunctional actions and reactions frequently result from contact between individuals and groups having different cultural lines of interpretation. Individuals and groups with left-shifted cultural lines of.interpretation such as, for example, culture 1, generally misinterpret right-shifted behavior along the entire spectrum as having significantly more positive meaning than it actually does coming from a group of individual from right-shifted culture such as for example, culture 3. Individuals and groups with right-shifted cultural lines of interpretation such as, for example, culture 3, generally misinterpret left-shifted behavior along the entire spectrum as having significantly more negative meaning than it actually does coming from a group or individual from a left-shifted society such as, for example, culture 1. This greatly contributes to cross-cultural misunderstanding, to the phenomenon of culture shock, and probably individual and/or group conflict.

Behaviors that can be indexed for the Behavioral Reference Indicia include basic interactive behaviors such as, for example, verbal and nonverbal communication, physical contact, collaboration and competition. These behaviors are plotted on Behavioral Reference Indicia axis 104 in FIGS. 1, 2 and 3 from the most negative to the most positive. The corresponding meanings or interpretations are plotted on the Interpretation Indicia axis 106 of FIGS. 1 and 2.

FIG. 2 demonstratively illustrates the variation in cultural interpretations of positive and negative behavior across left and right-shifted cultures. In culture 1, representing an individual or society with a left-shifted line of interpretation 102, the absence of communicative behavior represents a standard neutral interpretation (i.e., neither positive or negative), while in culture 3, which has the most right-shifted line of interpretation 204, the absence of communicative behavior between people in the course of daily conduct signifies a strongly negative interpretation such as, for example, disdain or hate. Culture 2 is an intermediate in which the absence of communicative behavior may have a mild or moderate negative interpretation such as, for example, disapproval. An individual or group from culture 1 interacting with cultures 2 and 3 may ignore others or show minimal signs of positive communicative behavior such as, for example, brief eye contact or smiling, and little or no verbal approval. While from the standpoint of the individual from the left-shifted culture 1 this has a neutral or somewhat positive meaning, individuals or groups in the right-shifted cultures 2 and 3 perceive this behavior as negative and, therefore, the individual or group is misinterpreted as being, for example, arrogant or even hateful (depending on the degree of right shift of the interpreting culture.)

As an expression of mildly negative meaning such as disapproval, people from left-shifted cultures may show verbal or nonverbal negative communicative behavior. Examples include a frown, a spoken warning, raised voice, yelling, or even physical contact such as pushing or hitting. The quantity and intensity of this negative behavior depends on both the amount of negative meaning or interpretation the behavior is intended to convey and on the degree of left shift of the individual's or group's line of interpretation and line of action.

In communication with right-shifted cultures, this behavior may be perceived as having significantly more negative meaning such as, for example, intense hate in which case significant and/or prolonged negative overreaction in response is likely to occur. Individuals or groups from left-shifted cultures can be mistakenly perceived as being uninhibited, hateful or irrational by right-shifted cultures. Conversely, an individual or group from a right-shifted culture trying to express disapproval or anger may only show absence of communication as a sign of disapproval. In interaction with a left-shifted culture, this may be misinterpreted as neutral conduct in which case there is a failure to respond adequately or respond at all.

On the more negative end of the Behavioral Reference Indicia spectrum, nonverbal and verbal warnings and threats coming from right-shifted individuals or groups, which represent strong disapproval, anger, or hate are misinterpreted by the culturally left-shifted individuals and groups as having only mild negative meaning or interpretation which leads to a failure to fully understand the magnitude of the warning and results in a significant under-reaction by the left-shifted individuals or groups. Along the entire Behavioral Reference Indicia spectrum, the same types of negative behavior are associated with comparatively greater negative emotions, meanings, and interpretations in right-shifted cultures than in left-shifted cultures. This also includes extreme forms of negative behavior such as physical violence and homicide, which have a comparatively greater negative meaning and are interpreted with greater negative emotion when performed in right-shifted cultures.

On the positive end of the Behavioral Reference Indicia spectrum, comparatively small quantities of positive behavior are required to establish a positive interpretation in left-shifted cultures. While in a left-shifted culture only positive nonverbal communication such as eye contact or collaboration on simple tasks may be required to establish, for example, friendship or sexual interest, a right-shifted society requires more extensive positive communicative behavior including, for example, conversation, physical contact, or more extensive cooperation. Establishing very positive sentiments and relationships such as strong friendship in left-shifted cultures may require only positive verbal communication or cooperation on moderately complex tasks. To establish the same relationship in a right-shifted culture, more extensive positive behavior is required such as prolonged cooperation on elaborate tasks.

An individual from a left-shifted culture attempting to express mild positive sentiments such as superficial friendship or politeness may be misinterpreted by a right-shifted culture as neutral or even somewhat negative or evasive. In attempting to communicate strongly positive meaning such as, for example, friendship or sexual interest, a culturally left-shifted individual may be misinterpreted as being only formally polite. In interpreting right-shifted behavior, a left-shifted individual or group may perceive formal politeness or superficial friendship manifested by positive gestures or conversation as indicating strong friendship or sexual interest. This may lead to a significant positive overreaction. Generally, the same types of positive behaviors are associated with comparatively greater positive emotions and meanings in left-shifted cultures than in right-shifted cultures along the entire spectrum.

FIG. 2 further illustrates a horizontal veto line 206 which can be described as a limiting threshold of negative behaviors below which a greatly increased probability of breakdown of reciprocated relationship occurs. Behaviors interpreted as being above the veto line 206 will generally result in attempts to moderate the response with regard and respect to the other party's emotions and decision making. Behaviors interpreted as falling below the veto line 206 greatly increase the probability of disregard for the other party's well being, emotions and decision making when formulating a responsive behavior. This can lead to unmoderated negative responses which can include repeated negative actions that are disproportionate to the offending behavior and/or planning or performing a single overwhelming action designed to extinguish the offending behavior or eliminate the opposing individual or group. The greater a culture is right-shifted, progressively smaller amounts of negative behaviors are required to cross the veto line 206 and cause a breakdown of moderated responsive behavior.

Figure 3:
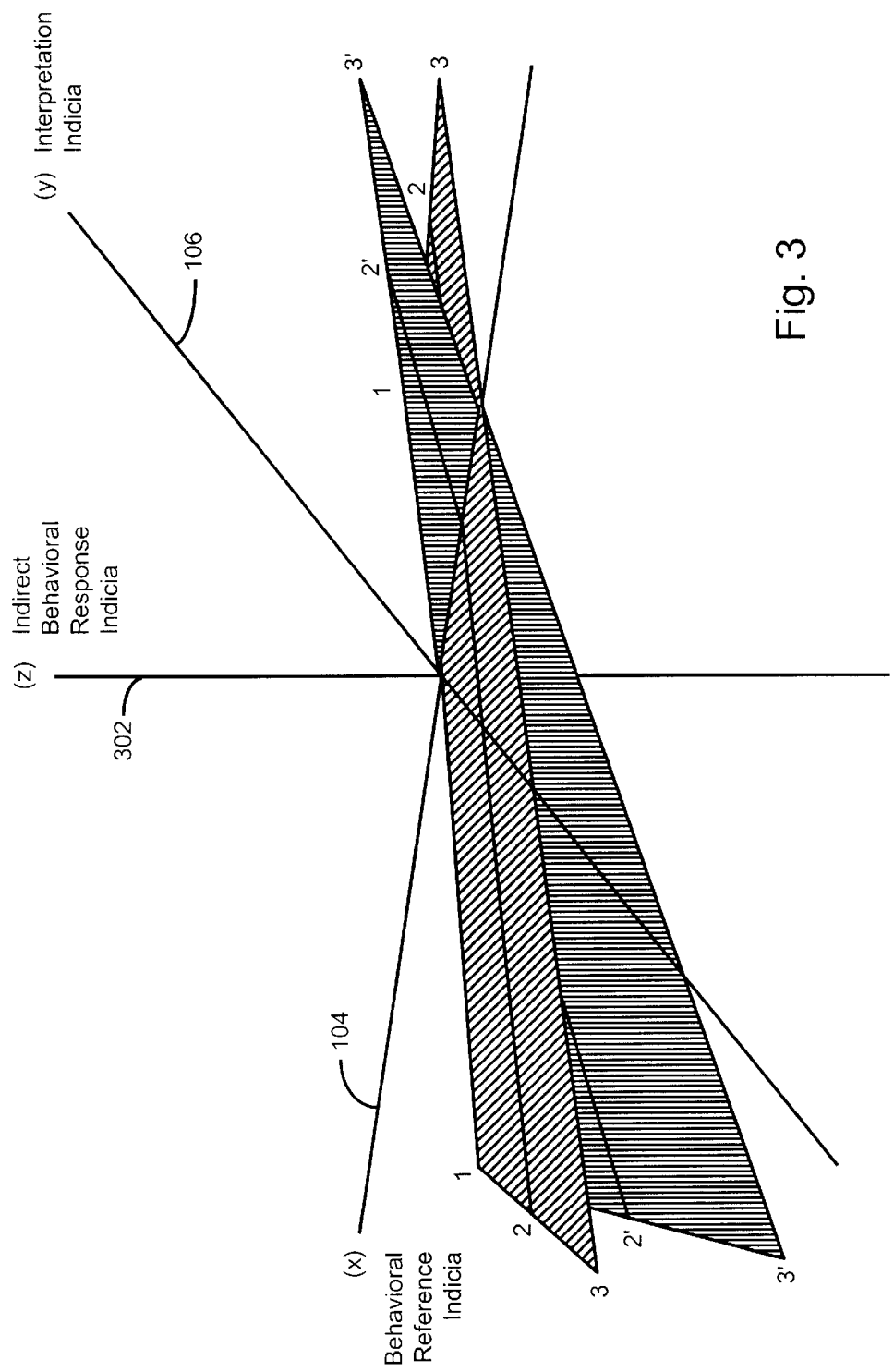
FIG. 3 is a graph illustrating a plurality of cultural lines of interpretation generated by plotting Behavioral Reference Indicia versus covert/overt Indirect Behavioral Response Indicia.

Referring now to FIG. 3, a three-dimensional graph plotting Indirect Behavioral Response Indicia (i.e., z-axis) versus Behavioral Reference Indicia (i.e., x-axis) and Interpretation Indicia (i.e., y-axis) is shown. In FIG. 3, a plurality of representative cultural lines of interpretation are shown such as, for example, cultural line of interpretation 1—1, 2—2, 3—3, 2'—2', and 3'—3'. Cultural lines of interpretation 1—1, 2—2, and 3—3 are shown in FIG. 3 with respect to the Behavioral Reference Indicia (i.e., x-axis) and Interpretation Indicia (i.e., y-axis) only. Cultural lines of interpretation 2'—2' and 3'—3' correspond to cultural lines of interpretation 2—2 and 3—3 as projected into the third dimension (i.e., Indirect Behavioral Response Indicia or z-axis). The three-dimensional graph of FIG. 3 is meant to illustrate the varying three-dimensional nature of the cultural lines of interpretation of the present invention.

In this regard, with increasing right shift in a cultural line of interpretation, there is a progressively greater negative interpretation (i.e., Interpretation Indicia) of negative behaviors (i.e., Behavioral Reference Indicia) and progressively decreasing social acceptability of all negative behaviors as a part of direct or overt behavior (i.e., Indirect Behavioral Response Indicia). As a result, in cultures with right-shifted lines of interpretation such as, for example, the culture represented by line of interpretation 3—3 and 3'—3', there is a decrease in relative proportion of negative behavior manifested as direct and/or overt behavior and a corresponding increase in proportion of negative behavior manifested as indirect and/or covert behavior. This indirect and/or covert behavior falls in the category of the third dimension behavior (e.g., z-axis in a conventional x, y, and z coordinate system), wherein the Behavioral Reference Indicia is the first dimension (e.g., x-axis).and the Interpretation Indicia is the second dimension (e.g., y-axis). The Interpretation Indicia is also an indicia that corresponds to direct or overt behavior responsive to the original or communicative behavior. The third dimension behavior, also referred to herein-after as the Responsive Behavior Indicia, can be defined as all negative and positive actions or reactions, individual or organized, legal or illegal that are conducted in an indirect and/or covert manner. For example, civil litigation or legal prosecution are third dimension behavior since these actions are conducted through the legal system and are therefore indirect. In the course of a society's abandonment of a left-shifted culture and the acquisition of right-shifted interpretation and behavior patterns, a decrease in the incidence of all forms of negative behavior enacted openly and directly and a concomitant increase in planning and enaction of negative behaviors done in a covert or indirect way is observed. This includes even extreme forms of negative behavior such as, for example, physical violence and homicide, which in a left-shifted culture are more likely to be direct or overt behavior while in a right-shifted culture they are more covert and/or indirect.

Referring now to FIGS. 2 and 3, an example of a cross-cultural type of interaction leading to third dimension behavior (i.e., behavior represented by an Indirect Behavioral Response Indicia) would be an individual or group from a right-shifted culture 3 being verbally threatened or physically assaulted by an individual or group from left-shifted culture 1. In this situation, the meaning perceived by the individual or group from the right-shifted culture 3 is greatly more negative than the meaning intended by the individual or group from the left-shifted culture 1. The response may be immediate and direct with the emotional intensity meaning of the response being much greater than the initial offending action. However, the response may also be toned down in the immediate setting. In either situation, subsequent reaction may include behaviors that are represented by Indirect Behavioral Response Indicia such as, for example, legal or illegal prosecution, private or public denunciation, individual or organized planning of action against the offending individual or group, etc. These responsive behaviors would constitute third dimension behavior since they are indirect and/or covert. The overall negative reaction is likely to be significantly greater in intent and magnitude than the initial action. By contrast, the expected response from a culturally left-shifted individual or group, as opposed to the presently discussed right-shifted individual or group, would more likely be direct and overt (e.g., verbal or physical response) and associated with comparatively less negative emotion, meaning, and interpretation. Consequently, there would be little or no subsequent third dimension behavior (i.e., none or low Indirect Behavioral Response Indicia.)

With an increasing right-shift in interpretation and behavior patterns, there is an increasing proportion of positive cooperative behaviors performed in a covert and/or indirect manner, as a part of third dimension behavior. The magnitude is correlated to the positive side of the Indirect Behavioral Response Indicia axis. Right-shifted cultures are, therefore, characterized by decreased public expression of friendship, affection and cooperation and an increased proportion of these behaviors performed in private, covert and/or indirect ways. Increasing cultural right shift generally leads to the development of extensive public and private institutions that allow for indirect expression of positive emotions and relationships and cooperative behavior. It is also expected to induce the development of secret organizations, groups, meetings, etc., which allow for positive relationships to be expressed and cooperative behavior to be performed in a covert manner.

Generally, with an increasing cultural right-shift, the spectrum of both positive and negative behaviors permitted to be done in a direct or open manner becomes progressively narrowed. There is a concomitant displacement of behaviors into the third dimension beginning from the most extreme ends of the positive and negative spectrum and continuing to include more and more moderate behaviors from each end. Therefore, extreme right-shift leads to the prohibition of direct expression and public display of all behaviors, except a very narrow range of those which designate exact neutrality. Furthermore, with increasing right-shift, progressively greater amounts of positive behavior are required to maintain neutral interpretations and none or low Indirect Behavioral Response Indicia.

Figure 4:
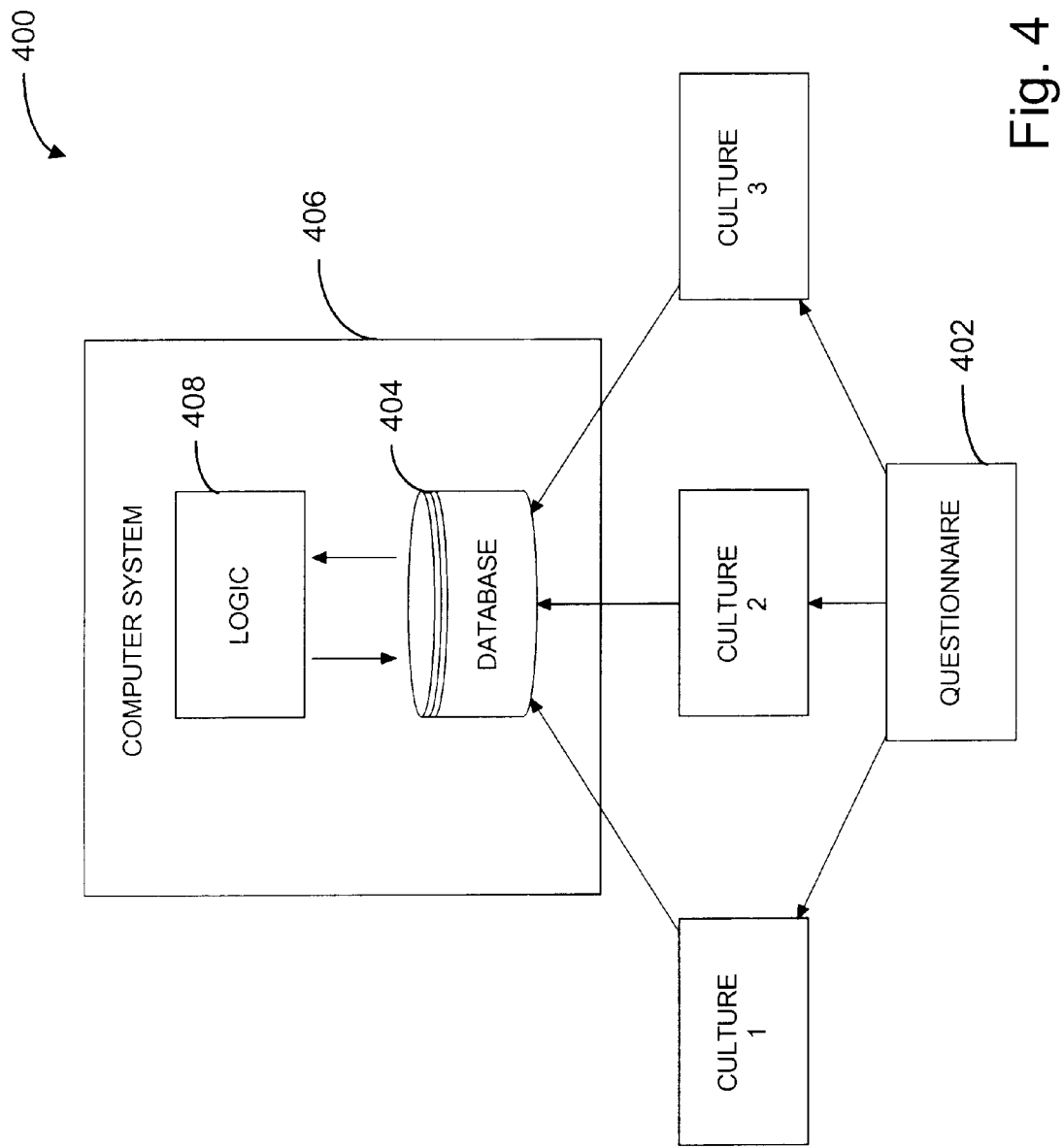
FIG. 4 is a functional block diagram illustrating a system for acquiring and utilizing data gathered from a plurality of cultures according to the present invention.

Referring now to FIG. 4, a system 400 for acquiring data necessary to establish the Behavioral Reference Indicia, Interpretation Indicia as well as the corresponding Direct Behavior Indicia, Indirect Behavioral Response Indicia, and Veto threshold is shown. In particular, specifically formulated questionnaires 402 are distributed to one or more cultures (e.g., culture 1, culture 2, culture 3, etc.) for answering. The method of distribution can manual or electronic. Electronic distribution preferably includes using either Email or the Internet. In this manner, data regarding a wide range of cultures can be economically acquired. The preferred embodiment of the questionnaire includes, for example, a question requesting identification of culture by country or nationality of the individual answering the questionnaire 402. The questionnaire 402 further includes a plurality of questions describing certain behaviors that are answered by indicating how the individual interprets the behavior and whether the individual would respond to the behavior in some direct or indirect manner. Table 1 below illustrates a representative question from a sample questionnaire 402.

TABLE 1

| Behavior Description | How would you Interpret this behavior? (−10 being strongly negative, 0 being neutral, 10 being strongly positive) | | | | | | | | | | | | | | | | | | | | | How would you respond to the described Behavior? | If your response is indirect, would it be overt or covert? |
|---|---|---|---|---|---|---|---|---|---|---|---|---|---|---|---|---|---|---|---|---|---|---|---|
| (Behavior 1) | −10 | −9 | −8 | −7 | −6 | −5 | −4 | −3 | −2 | −1 | 0 | 1 | 2 | 3 | 4 | 5 | 6 | 7 | 8 | 9 | 10 | Direct or Indirect | Overt or Covert |
| (Behavior 2) | −10 | −9 | −8 | −7 | −6 | −5 | −4 | −3 | −2 | −1 | 0 | 1 | 2 | 3 | 4 | 5 | 6 | 7 | 8 | 9 | 10 | Direct or Indirect | Overt or Covert |
| (Behavior N) | −10 | −9 | −8 | −7 | −6 | −5 | −4 | −3 | −2 | −1 | 0 | 1 | 2 | 3 | 4 | 5 | 6 | 7 | 8 | 9 | 10 | Direct or Indirect | Overt or Covert |

In the questionnaire 402, the Behavioral Description such as Behavior 1 may be phrased as follows "A person you know smiles at you." The individual responding to the questionnaire and the description of Behavior 1 would then circle an interpretation value in the range of −10 (i.e., strongly negative) to zero (0) (i.e., neutral) to +10 (i.e., strongly positive). The individual would then further indicate whether they would respond to the describe behavior directly or indirectly. This response may further be defined by a range. For example, the direct or indirect behavior may further be characterized by a range −10 (i.e., strongly negative) to zero (0) (i.e., neutral) to +10 (i.e., strongly positive). Alternatively or in addition, video presentations of the behavior description may be presented to the individual(s) for response to the questionnaire. The advantage of a video presentation of the behavioral description is that is conveys more precisely the communicative behavior than mere words on a questionnaire.

As described, an objective numerical scoring system can be assigned to the interactive behaviors based on the sum of the quantity of observed behaviors added to a numerical score of their duration and intensity (e.g., measured loudness of voice, etc.) Such numerical scores.or indicia are then plotted on the x-axis of a conventional x, y, and z coordinate system. Behaviors corresponding to the numerical score or indicia can then be stored on video (e.g., analog or digital) and subjectively evaluated or interpreted by individuals from different cultures. The evaluations or interpretations are assigned an interpretation or meaning indicia (+10 to −10, +100 to −100, etc.) Cross-cultural comparisons can then be made based on gender, age, socioeconomic status, geographic location and other parameters. Test subjects from different cultures can also be placed in live interactive situations and asked to rate their experience afterwards as either positive, neutral, or negative. Subjective quantification of positivity and negativity can be done on a numerical scale (1 to 10, 1 to 100, etc.) In addition, test subjects from different cultures can be placed in different interactive situations and their emotional arousal measured by monitoring vital signs, electrodermal response, etc. Under certain circumstances, expected results would include increase levels of emotional arouse with perceived interactive relationship extremes (e.g., negative as well as positive). Also, it would be expected that maintenance of low levels of arousal (i.e., a baseline state) would require progressively greater quantities of positive behavior with increasing cultural right shift.

The above-described description of behaviors, interpretations and responses to the described behaviors that appear on the questionnaire, or presented in combination with the questionnaire (e.g., video), are merely intended to be representative. Researchers and those having skill in the art may formulate other behavioral descriptions based on the teachings described herein. From the teachings of the present invention, it should be evident that an unlimited range of behaviors can be described or analyzed.

Once the questionnaire 402 has been completed, the information therein is used to form a database 404 in a computer system 406. The computer system 406 is preferably a personal computer system or a networked computer system with Internet capability. One embodiment of the organization of database 404 is shown in FIG. 5. More specifically, database 404 is preferably organized first by culture (i.e., Culture 1, Culture 2, etc.). Within each culture, a plurality of Behavior descriptions (i.e., Behavior 1, Behavior 2, ..., Behavior (N)) and their corresponding Behavioral Reference Indicia, Interpretation Indicia, and Indirect Behavioral Response Indicia are stored. As mentioned earlier, these indicia are derived directly from the responses to the questionnaires. For example, the indicia may be represented by the mean or median response to each question. Alternatively, the indicia may be represented by the median, mean, or the answer with the largest number of occurrences. The aforementioned indicia are preferably stored as values ranging from −10 to zero (0) to +10, which can then be easily converted to probabilities (e.g., 0=0%, −10 and +10=100%). The Behavioral Reference Indicia is determined based on the range of behavioral description. For example, a behavioral description characterized as "A person you know smiles at you" would presumably have a lesser positive Behavioral Reference Indicia than a behavior description characterized as "A person you know smiles at you and gives you a verbal complement." This is because the latter behavior includes additional positive behavior (i.e., "gives you a verbal complement.")

The database 404 may further include a veto threshold identification (if one has been determined for the particular behavior) field for each behavior that can take the form of entries indicating whether the interpretation indicia is above or below a determined threshold value. So configured, the database 404 is used by logic 408 to predict the culture-based interpretation (i.e., probability of positive, neutral, or negative interpretation) and direct and indirect response (i.e., probability of positive, neutral, or negative direct or indirect behavior) to a particular behavior.

Figure 7:
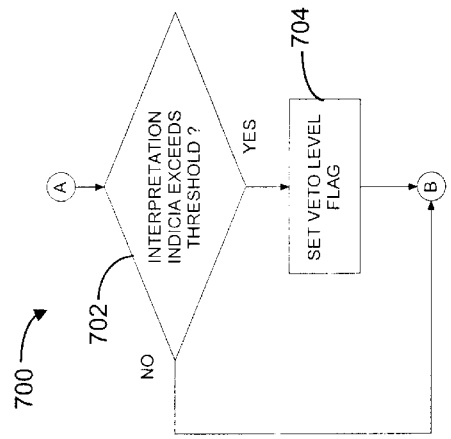
FIGS. 6 and 7 are flow charts illustrating one embodiment of the steps or logic of the present invention used to predict human behavior.
Figure 6:
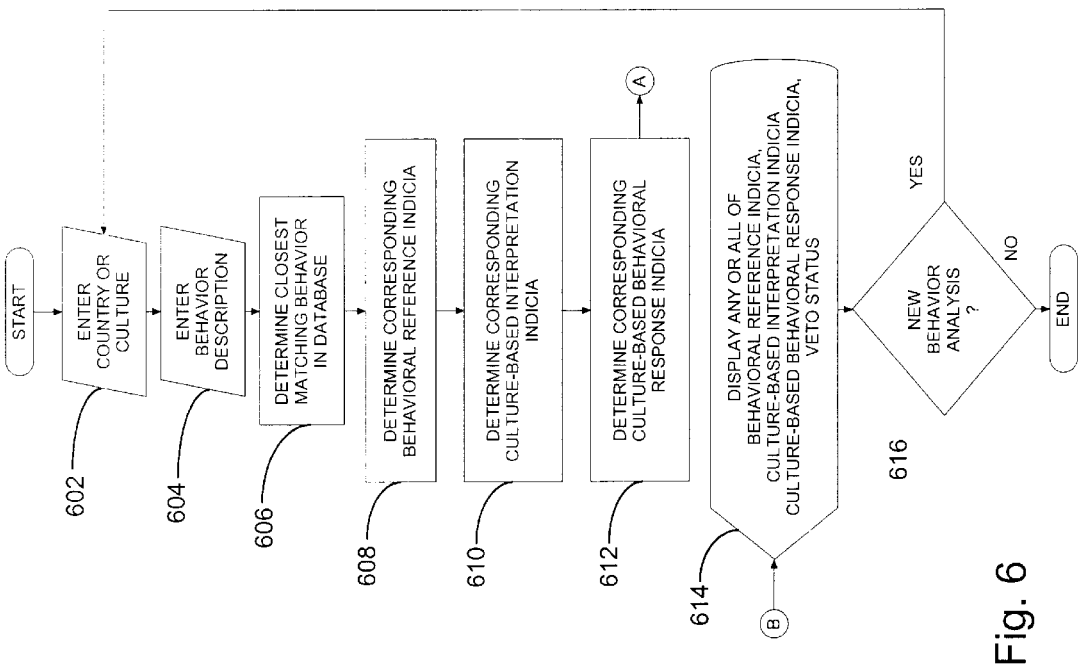

Referring now to FIGS. 6 and 7, the logic 408 for predicting human behavior is illustrated in the form of flowcharts 600 and 700. Referring specifically to FIG. 6, the logic starts in step 602 where the culture to used as the frame of analysis is entered. For example, culture can nationally based such as for example, Chinese, Russian, French, or German. After step 602, the logic requests input in step 604 of a description of the behavior to be analyzed within the identified culture. In step 606, the logic determines the closest machining behavioral description in database 404 by attempting to match as many as the key words appears in the input description with the database behavioral description. Once the input behavioral description is matched to a database behavioral description, the corresponding Behavioral Reference Indicia, culture-based Interpretation Indicia, and culture-based Indirect Behavioral Response Indicia in steps 608, 610, and 612, respectively.

After step 612, the logic may optionally proceed to step 702 of FIG. 7. In step 702, the Interpretation Indicia is compared a determined veto threshold level (if one has been determined). Alternatively, the veto threshold level identification field of database 404 may be used to determine if the veto threshold level has been exceeded. If the veto threshold level has been exceeded, the logic advances to step 704 where a veto level flag is set. After step 702, or if the veto threshold level has not been exceeded, the logic advances to step 614. In step 614, the logic displays on a display device such as, for example, a computer monitor, any or all of the Behavioral Reference Indicia, culture-based Interpretation Indicia (i.e., probability of positive or negative interpretation), culture-based Indirect Behavioral Response Indicia (i e., probability of positive or negative direct or indirect responsive behavior), and the veto threshold level status (i.e., exceeded or not.) For example, one such display may appear as follows:

| Culture: | Behavior: | Cultural Interpretation | Indirect Responsive Behavior | Veto Threshold |
|---|---|---|---|---|
| Culture 1 | A person you know smiles at you. | 90% Positive | 10% Positive | Not Exceeded |

After step 614, the logic advances to step 616 where it determines if new behavior is to be analyzed. If a new behavior is to be analyzed, the logic loops back to step 602. Otherwise, the logic flow ends.

While the present invention has been illustrated by the description of embodiments thereof, and while the embodiments have been described in considerable detail, it is not the intention of the applicants to restrict or in any way limit the scope of the appended claims to such detail. Additional advantages and modifications will readily appear to those skilled in the art. For example, the types of cultures to be analyzed may be defined by characteristics other than nationality such as for example, religion, profession, or other socially-based characteristics. Moreover, with further investigation, the present invention may be useful to predict illness or medical conditions. For example, the there may be a correlation between the shiftedness of a cultural line with an illness or medical condition. Additionally, the present invention may take the form of a computer-readable medium such as, for example, a magnetic disks, read-only memories (ROMs), programmable read-only memories (PROMs), electronically programmable read-only memories (EPROMs), electronically erasable programmable read-only memories, and compact-disk read-only memories (CD-ROMs). Therefore, the invention, in its broader aspects, is not limited to the specific details, the representative apparatus, and illustrative examples shown and described. Accordingly, departures may be made from such details without departing from the spirit or scope of the applicant's general inventive concept.

I claim:

1. A culture-based method of predicting human behavior comprising the steps of:
   (a) identifying a culture to be analyzed; wherein this step comprises reading a cultural description input and searching a database of cultural descriptions for a match;
   (b) identifying a behavioral communication;
   (c) associating the identified behavioral communication with a behavioral reference indicia;
   (d) associating the behavioral reference indicia with a culture-based covert behavior response indicia indicative of the probability of a covert behavior response to the identified behavioral communication; and
   (e) outputting the culture-based covert behavior response indicia for display.

2. The method of claim 1 wherein step (b) comprises the step of inputting a keyword description of the behavioral communication.

3. The method of claim 1 wherein step (b) comprises the step of selecting a behavioral communication from a predetermined list of behavioral communications.

4. The method of claim 1 wherein step (e) comprises the step of outputting the culture-based behavioral response indicia in the form of a percentage of probability of occurrence.

5. The method of claim 1 further comprising the step of identifying if a veto interpretation threshold has been exceeded.

6. The method of claim 5 wherein the step of identifying if a veto interpretation threshold has been exceeded comprises the step of identifying a culture-based interpretation indicia and comparing the interpretation indicia to an interpretation threshold.

7. A computer system for the culture-based prediction of the probability of a behavior in response to an observed behavior, the system comprising:
   (a) a database having at least one cultural description and at least one corresponding behavior description, behavioral reference indicia, and covert behavioral response indicia;
   (b) logic for predicting the probability of a covert behavior in response to the observed behavior, the logic comprising:
      (1) logic for identifying a culture to be analyzed;
      (2) logic for identifying an observed behavior;
      (3) logic for associating the identified behavior with a behavioral reference indicia;
      (4) logic for associating the behavioral reference indicia with a culture-based covert behavior response indicia indicative of the probability of a covert behavior in response to the identified behavior; and
      (5) logic for outputting the culture-based covert behavior response indicia for display.

8. The system of claim 7 wherein the logic for identifying an observed behavior comprises logic for inputting a keyword description of the behavior.

9. The system of claim 7 wherein the logic for identifying an observed behavior comprises logic for selecting a behavior from a predetermined list of observed behaviors.

10. The system of claim 7 wherein the logic for outputting the culture-based behavior response indicia for display comprises logic for outputting the culture-based behavioral response indicia in the form of a percentage of probability of occurrence.

* * * * *